(12) United States Patent
Mullane et al.

(10) Patent No.: US 8,695,589 B2
(45) Date of Patent: Apr. 15, 2014

(54) INHALER ASSIST DEVICE

(76) Inventors: Anthony J. Mullane, Colorado Springs, CO (US); William Ray Blessing, Jr., Manitou Springs, CO (US); Louis Douglas Shields, Colorado Springs, CO (US)

( * ) Notice: Subject to any disclaimer, the term of this patent is extended or adjusted under 35 U.S.C. 154(b) by 50 days.

(21) Appl. No.: 13/312,286

(22) Filed: Dec. 6, 2011

(65) Prior Publication Data

US 2013/0139814 A1    Jun. 6, 2013

(51) Int. Cl.
*A61M 11/00* (2006.01)
*A61M 15/00* (2006.01)

(52) U.S. Cl.
USPC ................................ 128/200.23; 128/200.14

(58) Field of Classification Search
USPC ............ 128/200.14–200.23, 203.12, 203.15; 222/472–474, 635
See application file for complete search history.

(56) References Cited

U.S. PATENT DOCUMENTS

| | | | |
|---|---|---|---|
| 4,834,083 A | 5/1989 | Byram et al. | |
| 4,953,545 A | 9/1990 | McCarty | |
| 4,972,830 A * | 11/1990 | Wong et al. | 128/200.21 |
| 5,184,761 A | 2/1993 | Lee | |
| 5,427,089 A | 6/1995 | Kraemer | |
| 6,257,231 B1 | 7/2001 | Shick et al. | |
| 6,345,617 B1 | 2/2002 | Engelbreth et al. | |
| 6,397,837 B1 | 6/2002 | Ferris | |
| 6,453,900 B1 | 9/2002 | Barnes, Jr. et al. | |
| 6,595,205 B2 | 7/2003 | Andersson | |
| 6,681,763 B2 | 1/2004 | Ferris | |
| 6,857,427 B2 | 2/2005 | Ziegler et al. | |
| 7,201,164 B2 | 4/2007 | Grychowski et al. | |
| 7,360,537 B2 | 4/2008 | Snyder et al. | |
| 7,832,393 B2 * | 11/2010 | Vito | 128/200.23 |
| 2002/0121276 A1 * | 9/2002 | Genova et al. | 128/200.23 |
| 2003/0029447 A1 * | 2/2003 | Vito | 128/200.23 |
| 2006/0107949 A1 * | 5/2006 | Davies et al. | 128/200.23 |
| 2007/0074718 A1 | 4/2007 | Austin | |
| 2008/0087279 A1 * | 4/2008 | Tieck et al. | 128/200.23 |

FOREIGN PATENT DOCUMENTS

GB    2233236    1/1991
JP    200972563    11/2009

* cited by examiner

*Primary Examiner* — Kevin C Sirmons
*Assistant Examiner* — Valerie L Skorupa
(74) *Attorney, Agent, or Firm* — Welsh Flaxman & Gitler LLC

(57) ABSTRACT

The present invention is directed to an inhaler assist device shaped and dimensioned for supporting a metered dose inhaler and an associated anti-static chamber in a manner allowing for assisted compression of the metered dose inhaler to dispense a dosage therefrom. The inhaler assist device includes an L-shaped housing assembly pivotally connected to a lever actuator. The housing assembly includes a planar base wall and lateral side walls extending from base wall, wherein the base wall and the lateral side walls create a cavity shaped and dimensioned for receipt of the metered dose inhaler and an anti-static chamber.

10 Claims, 3 Drawing Sheets

INHALER ASSIST DEVICE

BACKGROUND OF THE INVENTION

1. Field of the Invention

The present invention relates to an inhaler assist device which supports different types of anti-static chambers.

2. Description of the Related Art

Because metered dose inhalers are often difficult to operate various devices for employing leverage to enhance the actuation of the metered dose inhalers have been developed. Often anti-static chambers must be used with metered dose inhalers making it cumbersome and even more difficult for operators to handle. The prior art devices have shortcomings which the present invention attempts to address through the development of the inhaler assist device useable with an anti-static chamber. In particular, the present invention addresses holding the anti-static chamber while aiding in actuation of a metered dose inhaler.

SUMMARY OF THE INVENTION

It is, therefore, an object of the present invention to provide an inhaler assist device shaped and dimensioned for supporting a metered dose inhaler and an associated anti-static chamber in a manner allowing for assisted compression of the metered dose inhaler to dispense a dosage therefrom. The inhaler assist device includes an L-shaped housing assembly pivotally connected to a lever actuator. The housing assembly includes a first housing leg and a second housing leg. The first housing leg includes a first end and a second end and the second housing leg includes a first end and a second end. The respective second ends of the first housing leg and the second housing leg are fixedly connected, and a first end of the lever actuator is pivotally secured to the first end of the first housing leg defining a hinge therebetween. The housing assembly includes a planar base wall and lateral side walls extending from base wall, wherein the base wall and the lateral side walls create a cavity shaped and dimensioned for receipt of the metered dose inhaler and an anti-static chamber clip. The lever actuator includes a planar base wall and lateral side walls extending from the base wall.

It is also an object of the present invention to provide an inhaler assist device wherein the lever actuator also includes a plurality of support cross members extending downwardly from the base wall and between the lateral side walls.

It is another object of the present invention to provide an inhaler assist device wherein the lever actuator includes first, second, and third support cross members extending downwardly from the base wall and between the lateral side walls.

It is a further object of the present invention to provide an inhaler assist device wherein the first cross member is formed at the first end of the lever actuator, the second cross member is formed for engagement with the metered dose inhaler, and the third cross member is formed on a side of the second cross member opposite the first cross member.

It is also an object of the present invention to provide an inhaler assist device wherein the third cross member extends inwardly further than the first cross member or the second cross member.

It is another object of the present invention to provide an inhaler assist device including a concave recess shaped and dimensioned for positioning of the metered dose inhaler, the concave recess being defined by the first cross member and the third cross member of the lever actuator, the base wall of the lever actuator between the first cross member and the third cross member, and the lateral side walls of the lever actuator between the first cross member and the third cross member.

It is a further object of the present invention to provide an inhaler assist device wherein the concave recess is further defined by the base wall and lateral side walls of the first housing leg adjacent the first end of the first housing leg.

It is another object of the present invention to provide an inhaler assist device wherein the anti-static chamber clip is composed of first, second, third and fourth connection points shaped and dimensioned for frictionally engaging the anti-static chamber.

It is a further object of the present invention to provide an inhaler assist device wherein the first and second connection points are upper edges of the lateral side walls as they extend along the second housing leg.

It is also an object of the present invention to provide an inhaler assist device wherein the third and fourth connection points are formed along the lateral side walls extending along the first housing leg and are inwardly extending members defining substantially linear contact surfaces substantially parallel to and facing the first and second connection points.

It is another object of the present invention to provide an inhaler assist device wherein the spacing between the first, second, third and fourth connection points is such that a first end of the anti-static chamber may be positioned therein with the first, second, third and fourth connection points are shaped and dimensioned for frictionally engaging the anti-static chamber.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

Figure 1:
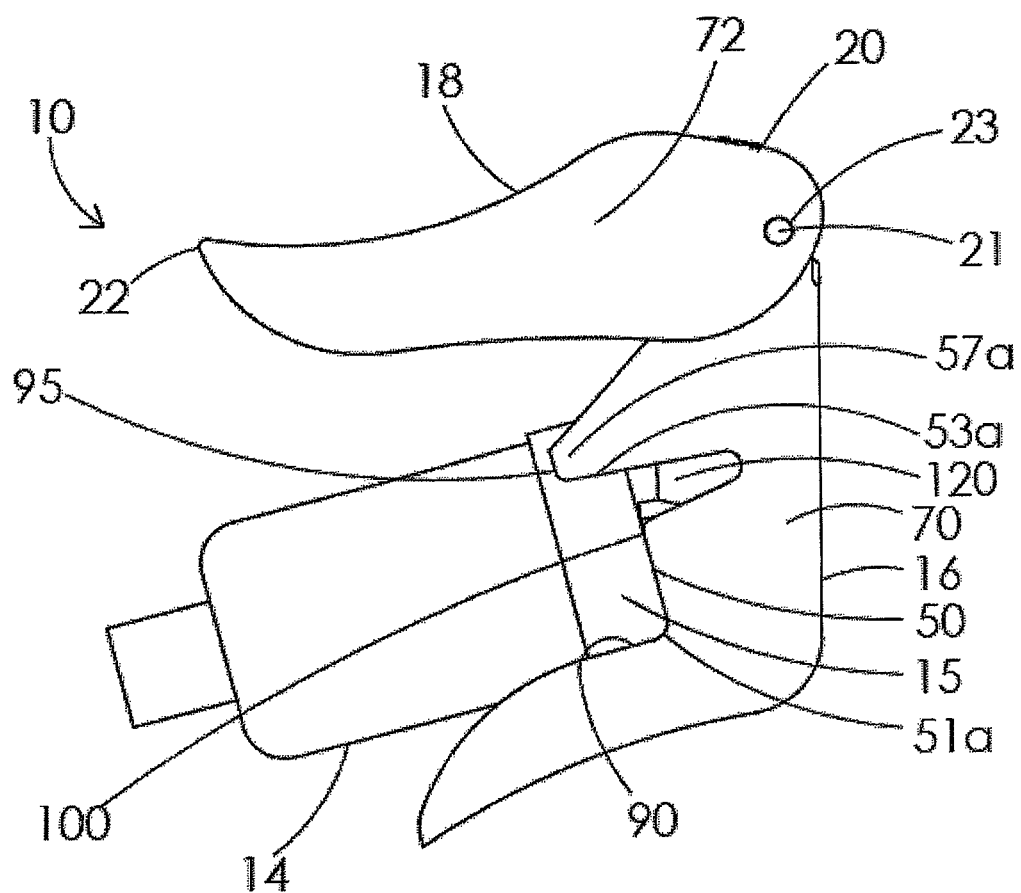
FIG. 1 is a side view of the present invention with an anti-static chamber attached.
Figure 2:
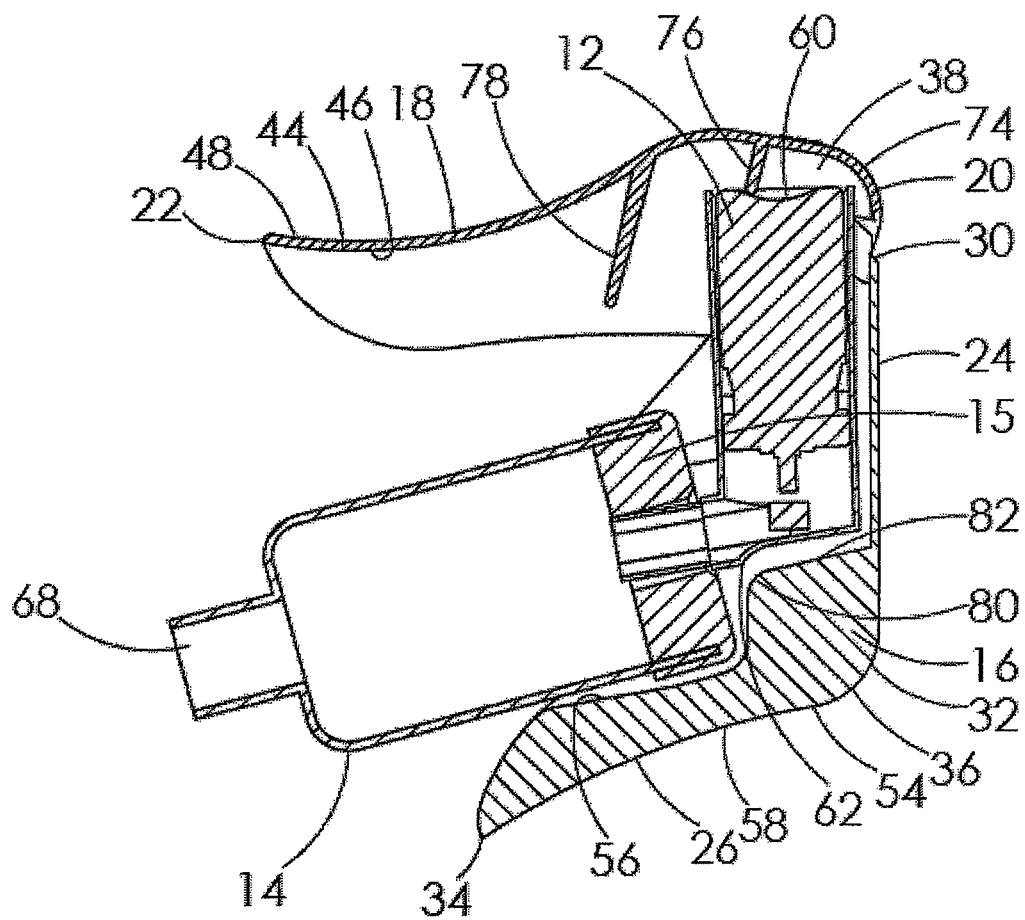
FIG. 2 is a cross sectional view taken along line 2-2 of FIG. 3.
Figure 3:
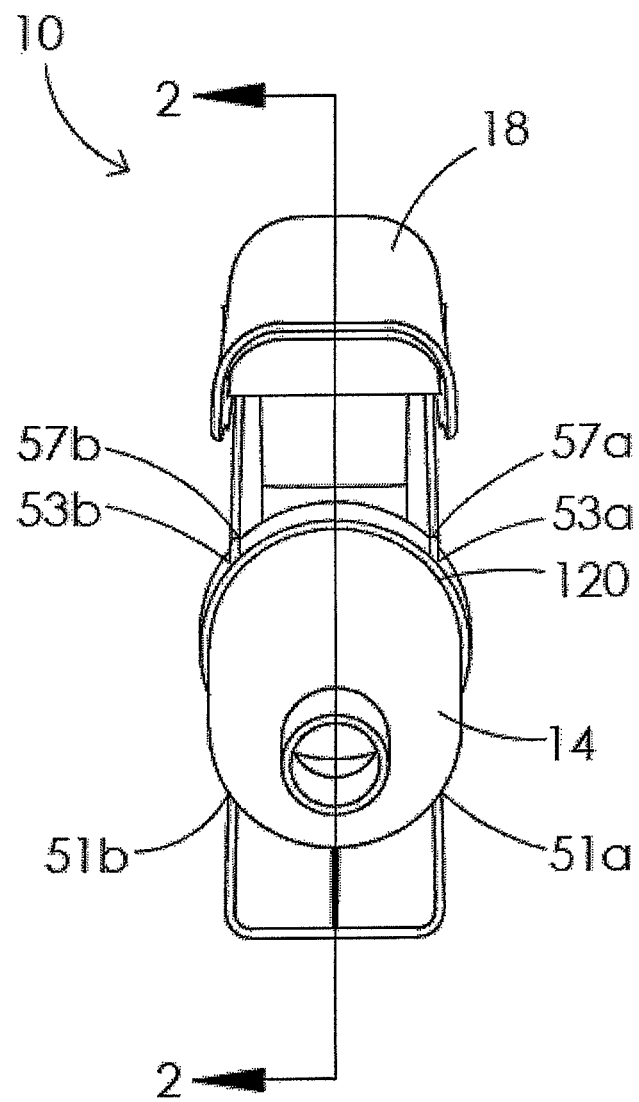
FIG. 3 is a front view of the present invention with an anti-static chamber attached.

In accordance with the present invention, and with reference to FIGS. 1 to 3, an inhaler assist device 10 is disclosed. The inhaler assist device 10 includes a housing assembly 16 pivotally connected to a lever actuator 18. The housing assembly 16 provides support for a metered dose inhaler 12 and anti-static chamber 14 as will be discussed below in greater detail. The lever actuator 18 includes a pivot first end 20 and a free second end 22.

The housing assembly 16 is substantially L-shaped and includes a first housing leg 24 and a second housing leg 26. The first housing leg 24 includes a first end 30 and a second end 32. The second housing leg 26 includes a first end 34 and a second end 36 which is common with second end 32 of first housing leg 24. The respective second ends 32, 36 of the first housing leg 24 and the second housing leg 26 are fixedly connected, and the pivot first end 20 of the lever actuator 18 is pivotally secured to the first end 30 of the first housing leg 24 by a pivot pin 21 to form a hinge 23.

The hinge 23 pivotally connects the first housing leg 24 with the lever actuator 18. A concave recess 38 is formed at the meeting point of the first housing leg 24 and the lever actuator 18. As will be discussed below in greater detail, the concave recess 38 is shaped and dimensioned for receiving the base or second end 60 of the metered dose inhaler 12 in a friction fit relationship. The concave recess 38 may be thought of as the combination and mating of the first end 30 of the first housing leg 24 and the first end 20 of the lever actuator 18.

More particularly, the housing assembly 16, in particular, the first housing leg 24 and the second housing leg 26, includes a base wall 54 with an inwardly facing surface 56 and an externally facing surface 58. The housing assembly 16 also includes lateral side walls 70 extending inwardly from base wall 54. As will be appreciated based upon the following disclosure, the combination of the base wall 54 and the lateral side walls 70 creates a cavity shaped and dimensioned for receipt of the metered dose inhaler 12 in the first housing leg 24. The lateral side walls 70 include a slot 120 which functions to allow the lateral side walls 70 to flex outward when an anti-static chamber 14 is press fit into the inhaler assist device 10.

Similarly, the lever actuator 18 includes a base wall 44 with an inwardly facing surface 46 and an externally facing top surface 48. The lever actuator 18 also includes lateral side walls 72 extending from base wall 44. As will be appreciated based upon the following disclosure, the combination of the base wall 44 and the lateral side walls 72 defines a generally U-shaped cavity. The lever actuator 18 also includes support cross members 74, 76, 78 extending downwardly from the base wall 44 and between the lateral side walls 72. The first cross member 74 is formed at the tip of the first end 20 of the lever actuator 18. A second cross member 76 is formed for engagement with the second end 60 of the metered dose inhaler 12 and a third cross member 78 is formed on the side of the second cross member 76 opposite the first cross member 74. The third cross member 78 extends inwardly further than the first or second cross members 74, 76 and functions to retain the second end 60 of the metered dose inhaler 12 in position within the lever actuator 18 by preventing lateral movement of the second end 60 of the metered dose inhaler 12 toward the free second end 22 of the lever actuator 18.

With the foregoing in mind, the concave recess 38 in which the second end 60 of the metered dose inhaler 12 is positioned is defined by the first and third cross members 74, 78 of the lever actuator 18, the base wall 44 of the lever actuator 18 between the first and third cross members 74, 78, and the lateral side walls 72 of the lever actuator 18 between the first and third cross members 74, 78. In addition, the concave recess 38 is further defined by the base wall 54 and lateral side walls 70 of the first housing leg 24 adjacent the first end 30 thereof.

The metered dose inhaler 12 is positioned, and frictionally fit, within the cavity defined by the base wall 54 and the lateral side walls 70 of the housing assembly 16 along the first housing leg 24, and extends between the concave recess 38 and the second housing leg 26 such that the application of pressure forcing the lever actuator 18 toward the second housing leg 26 will cause compression of the metered dose inhaler 12 to thereby dispense a dosage therefrom. Proper positioning of the metered dose inhaler 12 between the concave recess 38 and the housing assembly 16 is achieved by the provision of a shelf 80 at the junction of the first housing leg 24 and the second housing leg 26. The shelf 80 includes an upper support surface 82 shaped and dimensioned for engaging the dispensing, or first, end 62 of the metered dose inhaler 12.

In addition to housing the metered dose inhaler 12, the housing assembly 16 is particularly shaped and dimensioned to engage and retain an anti-static chamber 14 required to be used with a metered dose inhaler 12 by many users, with the metered dose inhaler 12 secured thereto. Anti-static chambers come in different shapes and sizes as such the inhaler assist device 10 is design to hold at least two different brands of anti-static chambers. As shown in the figures, and as those skilled in the art will certainly appreciate, the anti-static chamber 14 is frictionally secured to the dispensing end 62 of the metered dose inhaler 12. The anti-static chamber 14 is secured thereto at a transverse orientation relative to the longitudinal axis of the metered dose inhaler 12.

Attachment of the anti-static chamber 14, and ultimately the metered dose inhaler 12, to the housing assembly 16 is achieved by providing the housing assembly 16 with an anti-static chamber clip 50. The anti-static chamber clip 50 includes a clip recess 100. The anti-static chamber clip 50 is generally composed of four connection points comprised of 51a, 53a, and 51b, 53b (opposite 51a and 53a, respectively) shaped and dimensioned for frictionally engaging the coupled end 15 of the anti-static chamber 14. The four connection points 51a, 51b, 53a, 53b include first and second connection points 51a, 51b formed in lateral side walls 70 in the second housing leg 26 below the slot 120. In particular, the lateral side walls 70 include upper edges 90 which are parallel to each other and extend along a path substantially parallel to the a longitudinal axis of the second housing leg 26. Consequently, the upper edges 90 define support surfaces, that is, connection points 51a, 51b, upon which the outer wall of the anti-static chamber 14 may rest.

The anti-static chamber clip 50 is further provided with third and fourth connection points 53a, 53b defined by protrusions 57a and 57b on an upper portion of lateral side walls 70 formed extending along the first housing leg 24 above the slot 120. The third and fourth connection points 53a, 53b formed by protrusions 57a, 57b define substantially linear contact surfaces 95 substantially parallel to and facing the first and second connection points 51a, 51b. As such, the upper edges 90 and contact surfaces 95 of protrusions 57a, 57b define the clip recess 100 in which the anti-static chamber 14 is positioned for coupling with the inhaler assist device 10. The spacing between the first, second, third and fourth connection points 51a, 51b, 53a, 53b is such that the first end of the anti-static chamber 14 may be positioned therein with the connection points frictionally engaging the outer wall of the coupled end 15 of the anti-static chamber 14.

As briefly mentioned above, the lateral side walls 70 include a slot 120 which permits the anti-static chamber clip 50 to flex outward such that the four connection points 51a, 51b, 53a and 53b can grip a larger diameter anti-static chamber 14. As shown, the lateral side walls 70 are not flexed, but due to the slots 120 the lateral side walls 70 can flex outward, that is, with the second housing leg 26 moving away from the lever actuator 18, to accommodate a larger diameter anti-static chamber 14 which are still retained by the four connection points 51a, 51b, 53a and 53b.

Turning now to the lever actuator 18, the first end 20 of the lever actuator 18 is pivotally connected to the first end 30 of the first housing leg 24. As mentioned above, the junction of the first end 20 of the lever actuator 18 with the first end 30 of the first housing leg 24 defines the concave recess 38 shaped and dimensioned for placement of the base, or second, end 60 of the metered dose inhaler 12 while the dispensing, or first, end 62 of the metered dose inhaler 12 extends downward substantially in parallel alignment with the first housing leg 24 which ultimately joins the second end 36 of the second housing leg 26. While the concave recess 38 supports the base 60 of the metered dose inhaler 12, the lever actuator 18 is provided with an inwardly extending second cross member 76 for engaging the base 60 of the metered dose inhaler 12.

In practice, the first end of the anti-static chamber 14 (with the metered dose inhaler 12 secured thereto) is secured to the anti-static chamber clip 50 such that the longitudinal axis of the anti-static chamber 14 is in substantially parallel alignment with the longitudinal axis of the second housing leg 26 as it extends from its first end 34 to its second end 36. The metered dose inhaler 12 is thereby positioned within the recess defined by the base wall 54 and lateral side walls 70 along the second housing leg 26.

With the anti-static chamber 14 securely coupled to the housing assembly 16, the lever actuator 18 is rotated toward the second housing leg 26 until such a time that the base 60 of the metered dose inhaler 12 seats within the concave recess 38. The distance from the upper support surface 82 of the shelf 80 formed at the second end 36 of the second housing leg 26 to the base wall 44 of the lever actuator 18 adjacent the concave recess 38 is substantially the same as the length of the metered dose inhaler 12. As such the metered dose inhaler 12 fits snuggly between the second end 36 of the second housing leg 26 and the concave recess 38, in particular, the second cross member 76 of the lever actuator 18, when the lever actuator 18 is in its starting position (that is, the positioned of the lever actuator 18 when the metered dose inhaler 12 is loaded but the metered dose inhaler 12 has not been actuated for dispensing of a dose).

With the lever actuator 18 in its start position and the metered dose inhaler 12 positioned between the second end 36 of the second housing leg 26 and the concave recess 38 adjacent the first end 20 of the lever actuator 18, the user places his or her mouth over the discharge opening 68 of the anti-static chamber 14 and squeezes the second end 22 of lever actuator 18 toward the second housing leg 26. This will cause the application of pressure to along the length of the metered dose inhaler 12 causing the discharge of medicine therefrom.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An inhaler assist device shaped and dimensioned for supporting a metered dose inhaler and an associated anti-static chamber in a manner allowing selective coupling of the metered dose inhaler and anti-static chamber for assisted compression of the metered dose inhaler to dispense a dosage therefrom, the inhaler assist device comprising:
an L-shaped housing assembly pivotally connected to a lever actuator;
the housing assembly includes a first housing leg and a second housing leg, the first housing leg includes a first end and a second end and the second housing leg includes a first end and a second end, the respective second ends of the first housing leg and the second housing leg are fixedly connected, and a first end of the lever actuator is pivotally secured to the first end of the first housing leg defining a hinge therebetween;
the housing assembly includes a planar base wall and lateral side walls extending from the base wall, wherein the base wall and the lateral side walls create a cavity shaped and dimensioned for simultaneous selective coupling to both the metered dose inhaler and an anti-static chamber; wherein the lateral side walls of the housing include a slot forming a flexible anti-static chamber clip to accommodate different dimensioned anti-static chambers; and
the lever actuator includes a planar base wall and lateral side walls extending from the base wall, the lever actuator further including at least one support cross member extending downwardly from the planar base wall and between the lateral side walls of the lever actuator.

2. The inhaler assist device according to claim 1, wherein the lever actuator also includes a plurality of support cross members extending downwardly from the planar base wall and between the lateral side walls of the lever actuator.

3. The inhaler assist device according to claim 1, wherein the lever actuator includes first, second, and third support cross members extending downwardly from the planar base wall and between the lateral side walls of the lever actuator.

4. The inhaler assist device according to claim 3, wherein the first support cross member is formed at the first end of the lever actuator, the second support cross member is formed for engagement with the metered dose inhaler, and the third support cross member is formed on a side of the second support cross member opposite the first support cross member.

5. The inhaler assist device according to claim 4, wherein the third support cross member extends inwardly further than the first support cross member or the second support cross member.

6. The inhaler assist device according to claim 4, further including a concave recess shaped and dimensioned for positioning of the metered dose inhaler, the concave recess being defined by the first support cross member and the third support cross member of the lever actuator, the base wall of the lever actuator between the first support cross member and the third support cross member, and the lateral side walls of the lever actuator between the first support cross member and the third support cross member.

7. The inhaler assist device according to claim 6, wherein the concave recess is further defined by the planar base wall and lateral side walls of the first housing leg adjacent the first end of the first housing leg.

8. The inhaler assist device according to claim 1, wherein the anti-static chamber clip is composed of first, second, third and fourth connection portions shaped and dimensioned for frictionally engaging the anti-static chamber.

9. The inhaler assist device according to claim 8, wherein the first and second connection portions are upper edges of the lateral side walls of the housing below the slot as they extend along the second housing leg.

10. The inhaler assist device according to claim 8, wherein the third and fourth connection portions are formed along the lateral side walls of the housing above the slot and extend along the first housing leg and are inwardly extending members defining substantially linear contact surfaces substantially parallel to and facing the first and second connection portions.

* * * * *